United States Patent [19]

Boltze et al.

[11] 4,241,207
[45] Dec. 23, 1980

[54] ORGANONITROGEN DERIVATIVES OF 2-BENZOPYRANONE

[75] Inventors: Karl-Heinz Boltze, Bensberg-Kippekausen; Peter-Rudolf Seidel, Porz-Wahnheide; Haireddin Jacobi, Leichlingen; Helmut Schwarz, Bensberg-Frankenforst, all of Fed. Rep. of Germany

[73] Assignee: Troponwerke Dinklage & Co., Cologne, Fed. Rep. of Germany

[21] Appl. No.: 963,652

[22] Filed: Nov. 24, 1978

Related U.S. Application Data

[62] Division of Ser. No. 703,340, Jul. 8, 1976, Pat. No. 4,144,336.

[30] Foreign Application Priority Data

Jul. 8, 1975 [DE]  Fed. Rep. of Germany ....... 2530405
Oct. 2, 1975 [DE]  Fed. Rep. of Germany ....... 2543945

[51] Int. Cl.$^3$ ................. C07D 311/08; C07D 407/14
[52] U.S. Cl. .................................. 542/427; 542/421; 260/326.85; 260/343.45; 546/187
[58] Field of Search ............. 260/343.45, 326.85; 542/427, 416, 421; 546/187

[56] References Cited

U.S. PATENT DOCUMENTS 3,520,893  7/1970  Beyerle ................... 260/343.45
3,652,557  3/1972  Beyerle et al. ............ 260/343.45

Primary Examiner—Henry R. Jiles
Assistant Examiner—Jane T. Fan

Attorney, Agent, or Firm—Sprung, Felfe, Horn, Lynch & Kramer

[57] ABSTRACT

Novel 2-benzopyranone compounds of the formula

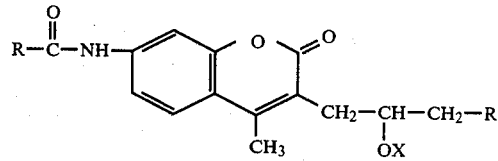

wherein
X is a 3,4,5-trimethoxybenzoyl group or a 3,4,5-trimethoxycinnamoyl group; and each
R individually is selected from the group consisting of alkylamino and dialkylamino in which one carbon atom in the alkyl moiety may be replaced by an oxygen atom and one hydrogen atom may be replaced by a hydroxyl group which may in turn be esterified with a 3,4,5-trimethoxybenzoyl or 3,4,5-trimethoxycinnamoyl group; amino substituted once or twice by alkenyl, aralkyl, or cycloalkyl; or a 4- to 7-membered N-containing heterocyclic ring linked through a nitrogen atom and which contains up to 3 hetero atoms, which heterocyclic ring may be substituted by phenyl, alkyl or hydroxyalkyl, wherein the hydroxy group may be esterfied by a 3,4,5-trimethoxy benzoyl or 3,4,5-trimethoxy cinnamoyl group;

or a salt of each compound with a physiologically acceptable acid; possess outstanding activity as coronary dilators. Processes for producing such compounds are also disclosed.

39 Claims, 3 Drawing Figures

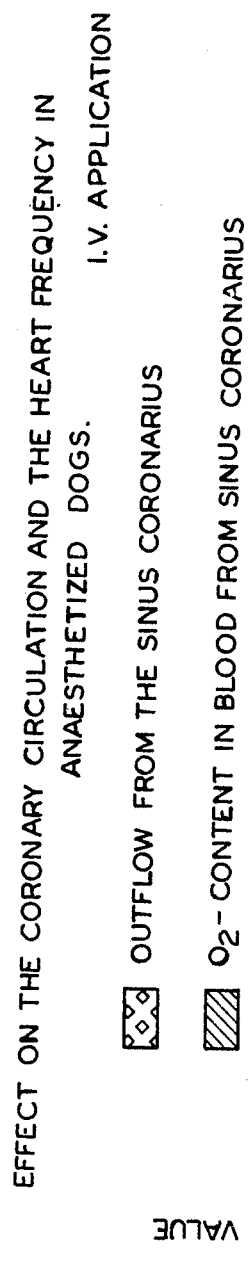

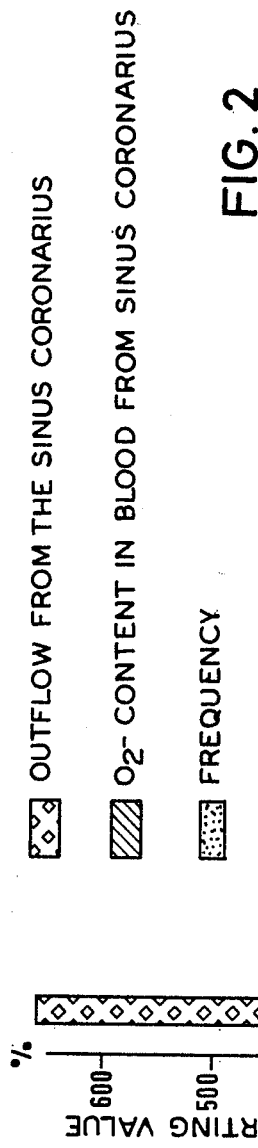

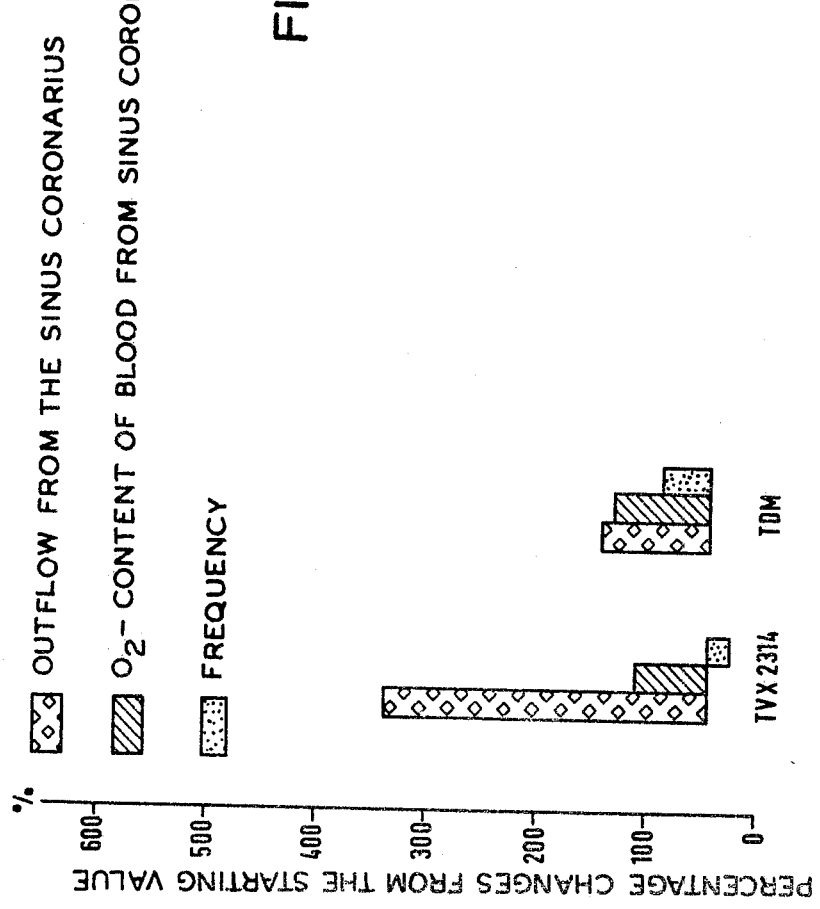

ORGANONITROGEN DERIVATIVES OF 2-BENZOPYRANONE

This is a division of application Ser. No. 703,340, filed July 8, 1976, U.S. Pat. No. 4,144,336.

This invention relates to new 2-benzopyranone derivatives, to a process for their production and to their use as medicaments, more especially as coronary dilators.

It is already known that 2-benzopyranone derivatives can be used inter alia as coronary dilators in human medicine. For example, α-[3-(2-diethylaminoethyl)-4-methyl-2-oxo-2H-1-benzopyran-7-yl]-hydroxy actic acid ethyl ester (I.N.N.=Carbocromen, hereinafter referred to as CBC) has long been used as a coronary dilator in human medicine and, when administered intravenously, produces a marked increase in circulation through the coronary arteries. When administered enterally, however, CBC has no effect upon coronary circulation (cf. D. Lorenz and H. D. Dell, 10th Spring Congress of the German Pharmacological Society, 16th to 19th March, 1969; Special Publication from Naunyn-Schmiedeberg's Arch. Pharmakol. 264 (1969), pages 272–275; D. Lenke, Arzneimittelforschung 20 (1970), pages 655), which is not surprising insofar as M. Klarwein et al (Arzneimittel-Forschung 15 (1965), page 555) had already been found that, when incubated in whole blood and in liver homogenate at a temperature of 37° C., CBC is degraded after only ten minutes to a level of 97 to 100% to form a coronary-inactive metabolite.

It has also been proposed to use N-[3-(2-morpholinoethyl)4-methyl-2-oxo-2H-1-benzopyran-7-yl]-4-morpholino carboxamide (hereinafter referred to as MMB, cf. German Offenlegungsschrift No. 2,035,536) as a coronary dilator. Although MMB has the advantage over CBC that it is also enterally active and is not enzymatically decomposed as quickly as CBC, it does show not only qualitatively, but also quantitatively, unfavourable differences in relation to the compounds according to the invention.

Finally, it has also been proposed to use 3,4,5-trimethoxy benzoic acid-[1-(7,8-dimethoxy-4-methyl-2-oxo-2H-1-benzopyran-3-yl)-3-morpholino-2-propyl ester] (hereinafter referred to as TDM; cf. S.A.P. No. 6900365; Chem. Abstracts 79 (1970); 100516 c). Unfortunately, this compound also shows some disadvantages in relation to the compounds according to the invention, as shown further on by the Comparison Tests. The above-mentioned compounds correspond to the formulae

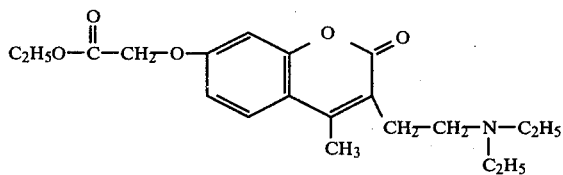

CBC

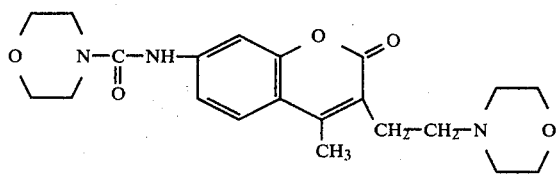

MMB

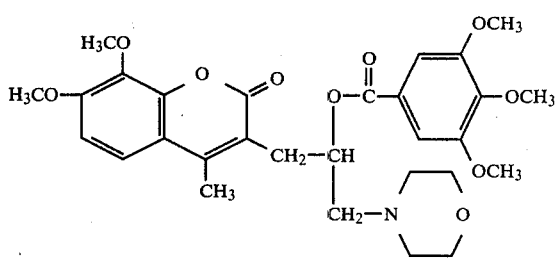

TDM

The present invention relates to new 2-benzopyranone derivatives corresponding to the general formula

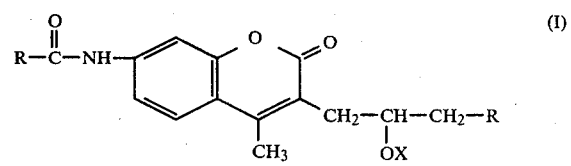

and their salts with physiologically acceptable acids. In formula I, X and R have the following meanings:

X represents a 3,4,5-trimethoxy benzoyl group or a 3,4,5-trimethoxy cinnamoyl group, and the two groups R which may be the same or different and are preferably the same represent an amino group which may be unsubstituted or substituted once or twice by alkyl radicals preferably containing from 1 to 6 carbon atoms, in which alkyl radicals one carbon atom may be replaced by an oxygen atom and in which one hydrogen atom may be replaced by a hydroxyl group which may in turn be esterified with a 3,4,5-trimethoxy benzoyl or 3,4,5-trimethoxy cinnamoyl group;

an amino group which may be substituted once or twice by alkenyl radicals preferably containing from 2 to 4 carbon atoms, by aralkyl radicals with preferably up to 10 carbon atoms or by cycloalkyl radicals preferably containing from 4 to 7 carbon atoms;

or a nitrogen atom which is a member of a 4-membered to 7-membered heterocyclic ring with up to 3 hetero atoms, preferably with 1 or 2 hetero atoms, the heterocyclic ring optionally being substituted by a phenyl radical or by an alkyl radical with preferably up to 3 carbon atoms or by a hydroxy alkyl radical preferably containing from 1 to 3 carbon atoms, the hydroxy group optionally being esterified by a 3,4,5-trimethoxy benzoyl or 3,4,5-trimethoxy cinnamoyl group. The preferred hetero atoms are nitrogen and oxygen.

The new compounds are suitable for use as medicaments and are distinguished in particular by their high activity in stimulating myocardial circulation.

It has also been found that the new 2-benzopyranone derivatives of general formula I can be obtained by reacting benzopyranone derivatives corresponding to the general formula

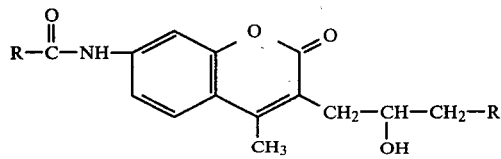

in which R is as defined above,
with 3,4,5-trimethoxy benzoyl halide or 3,4,5-trimethoxy cinnamoyl halide, more especially with the corresponding acid chloride, in the presence of acid-binding agents and optionally converting the compounds obtained into their salts with physiologically acceptable acids.

The compounds according to the invention surprisingly show greater and more persistent activity in stimulating myocardial circulation than the compounds known from the prior art.

The following compounds are mentioned as new active principles according to the invention:

N-{3-[3-(4-phenyl-1-piperazinyl)-2-(3,4,5-trimethoxybenzoyloxy)-propyl]-4-methyl-2-oxo-2H-1-benzopyran-7-yl}-4-phenyl-1-piperazinyl carboxamide;

N-{3-[3-(4-phenyl-1-piperazinyl)-2-(3,4,5-trimethoxycinnamoyloxy)-propyl]-4-methyl-2-oxo-2H-1-benzopyran-7-yl}-4-phenyl-1-piperazinyl carboxamide;

N-{3-[3-piperidine-2-(3,4,5-trimethoxycinnamoyloxy)-propyl]-4-methyl-2-oxo-2H-1-benzopyran-7-yl}-1-piperidinocarboxamide;

N-{3-[3-(2,6-dimethyl-4-morpholinyl)-2-(3,4,5-trimethoxycinnamoyloxy)-propyl]-4-methyl-2-oxo-2H-1-benzopyran-7-yl}-2,6-dimethyl-4-morpholinocarboxamide;

N-{3-[3-(2,6-dimethyl-4-morpholinyl)-2-(3,4,5-trimethoxybenzoyloxy)-propyl]-4-methyl-2-oxo-2H-1-benzopyran-7-yl}-2,6-dimethyl-4-morpholinocarboxamide;

N-{3-[3-(4-methylpiperidino)-2-(3,4,5-trimethoxybenzoyloxy)-propyl]-4-methyl-2-oxo-2H-1-benzofuran-7-yl}-4-methyl-1-piperidinocarboxamide;

N-{3-[3-piperidino-2-(3,4,5-trimethoxybenzoyloxy)-propyl]-4-methyl-2-oxo-2H-1-benzopyran-7-yl}-1-piperidinocarboxamide;

N-{3-[3-diallylamino-2-(3,4,5-trimethoxycinnamoyloxy)-propyl]-4-methyl-2-oxo-2H-1-benzopyran-7-yl}-N',N'-diallyl urea;

N-{3-[3-diethylamino-2-(3,4,5-trimethoxybenzoyloxy)-propyl]-4-methyl-2-oxo-2H-1-benzopyran-7-yl}-N',N'-diethyl urea;

N-{3-[3-diethylamino-2-(3,4,5-trimethoxycinnamoyloxy)-propyl]-4-methyl-2-oxo-2H-1-benzopyran-7-yl}-N',N'-diethyl urea;

N-{3-[3-(methylbenzylamino)-2-(3,4,5-trimethoxybenzoyloxy)-propyl]-4-methyl-2-oxo-2H-1-benzopyran-7-yl}-N'-benzyl-N'-methyl urea;

N-{3-[3-(methylbenzylamino)-2-(3,4,5-trimethoxycinnamoyloxy)-propyl]-4-methyl-2-oxo-2H-1-benzopyran-7-yl}-N'-benzyl-N'-methyl urea;

N-{3-[3-(cyclohexylmethylamino)-2-(3,4,5-trimethoxybenzoyloxy)-propyl]-4-methyl-2-oxo-2H-1-benzopyran-7-yl}-N'-cyclohexyl-N'-methyl urea;

N-{3-[3-(methylcyclohexylamino)-2-(3,4,5-trimethylcinnamoyloxy)-propyl]-4-methyl-2-oxo-2H-1-benzopyran-7-yl}-N'-cyclohexyl-N'-methyl urea;

N-{3-[3-morpholino-2-(3,4,5-trimethoxybenzoyloxy)-propyl]-4-methyl-2-oxo-2H-1-benzopyran-7-yl}-4-morpholinocarboxamide;

N-{3-[3-morpholino-2-(3,4,5-trimethoxycinnamoyloxy)-propyl]-4-methyl-2-oxo-2H-1-benzopyran-7-yl}-4-morpholinocarboxamide N-{3-[3-perhydroazepino-2-(3,4,5-trimethoxybenzoyl)-propyl]-4-methyl-2-oxo-2H-1-benzopyran-7-yl}-1-perhydroazepinocarboxamide;

N-{3-[3-perhydroazepino-2-(3,4,5-trimethoxycinnamoyloxy)-propyl]-4-methyl-2-oxo-2H-1-benzopyran-7-yl}-1-perhydroazepinocarboxamide;

N-{3-[3-pyrrolidino-2-(3,4,5-trimethoxybenzoyloxy)-propyl]-4-methyl-2-oxo-2H-1-benzopyran-7-yl}-1-pyrrolidinocarboxamide;

N-{3-[3-pyrrolidino-2-(3,4,5-trimethoxycinnamoyloxy)-propyl]-4-methyl-2-oxo-2H-1-benzopyran-7-yl}-1-pyrrolidinocarboxamide;

N-{3-[3-di-n-butylamino-2-(3,4,5-trimethoxybenzoyloxy)-propyl]-4-methyl-2-oxo-2H-1-benzopyran-7-yl}-N',N'-di-n-butyl urea;

N-{3-[3-di-n-butylamino-2-(3,4,5-trimethoxycinnamoyloxy)-propyl]-4-methyl-2-oxo-2H-1-benzopyran-7-yl}-N'-N'-di-n-butyl urea;

N-{3-[3-diallylamino-2-(3,4,5-trimethoxybenzoyloxy)-propyl]-4-methyl-2-oxo-2H-1-benzopyran-7-yl}-N',N'-diallyl urea;

N-{3-[3-(2-ethylpiperidino)-2-(3,4,5-trimethoxybenzoyloxy)-propyl]-4-methyl-2-oxo-2H-1-benzopyran-7-yl}-2-ethyl-1-piperidinocarboxamide;

N-{3-[3-(2-ethylpiperidino)-2-(3,4,5-trimethoxycinnamoyloxy)-propyl]-4-methyl-2-oxo-2H-1-benzopyran-7-yl}-2-ethyl-1-piperidinocarboxamide;

N-{3-[3-(4-methyl-1-piperazinyl)-2-(3,4,5-trimethoxybenzoyloxy)-propyl]-4 -methyl-2-oxo-2H-1-benzopyran-7-yl}-4-methyl-1-piperazinyl carboxamide;

N-{3-[3-(N-methyl-N-(3,4,5-trimethoxybenzoyloxyethyl)-amino)-2-2-(3,4,5-trimethoxybenzoyloxy)-propyl]-4-methyl-2-oxo-2H-1-benzopyran-7-yl}-N'-methyl-N'-(3,4,5-trimethoxybenzoyloxyethyl) urea;

N-{3-[3-(N-methyl-N-(3,4,5-trimethoxycinnamoyloxyethyl)-amino)-2-(3,4,5-trimethoxycinnamoyloxy)-propyl]-4-methyl-2-oxo-2H-1-benzopyran-7-yl}-N'-methyl-N'-(3,4,5-trimethylcinnamoyloxyethyl) urea;

N-{3-[3-(N-methyl-N-(3,4,5-trimethoxybenzoyloxyethoxyethyl)-amino)-2-(3,4,5-trimethoxybenzoyloxy)-propyl]-4-methyl-2-oxo-2H-1-benzopyran-7-yl}-N'-methyl-N'-(3,4,5-trimethoxycinnamoyloxyethoxyethyl) urea;

N-{3-[3-(N-methyl-N-(3,4,5-trimethoxycinnamoyloxyethoxyethyl)-amino)-2-(3,4,5-trimethoxycinnamoyloxy)-propyl]-4-methyl-2-oxo-2H-1-benzopyran-7-yl}-N'-methyl-N'-(3,4,5-trimethoxycinnamoyloxyethoxyethyl) urea;

N-{3-[3-{4-(2-(3,4,5-trimethoxybenzoyloxy)-ethyl)-1-piperazinyl}-2-(3,4,5-trimethoxybenzoyloxy)-propyl]-4-methyl-2-oxo-2H-1-benzopyran-7-yl}-4-(3,4,5-trimethoxybenzoyloxyethyl)-1-piperazinyl carboxamide;

N-{3-[3-{4-(2-(3,4,5-trimethoxycinnamoyloxy)-ethyl)-1-piperazinyl}-2-(3,4,5-trimethoxycinnamoyloxy)-propyl]-4-methyl-2-oxo-2H-1-benzopyran-7-yl}-4-(3,4,5-trimethoxycinnamoyloxyethyl)-1-piperazinyl carboxamide.

N-{3-[3-morpholino-2-(3,4,5-trimethoxybenzoyloxy)-propyl]-4-methyl-2-oxo-2H-1-benzopyran-7-yl}-morpholinocarboxamide (hereinafter referred to as TVX 2209, see Table 1, column 1 for this and the following test names "TVX") was subjected to exhaustive pharmacological tests as the prototype of the compounds according to the invention. After administration by intravenous injection to anaesthetised dogs, it was possible to show that TVX 2209 regularly produced a very marked, lasting increase in the output of blood from the coronary sinus (cf. Table 1). At the same time, there was a marked, lasting increase in the concentration of oxygen in the coronary sinus blood.

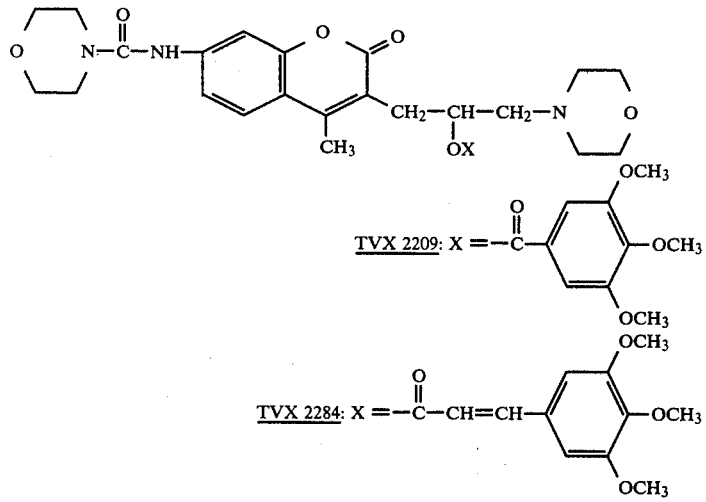

It was also possible, in the case of anaesthetised dogs, to show that the compounds are also active after intraduodenal administration, i.e. are enterally resorbed to an adequate extent. TVX 2209 and its derivatives are so-called benign coronary dilators because, on the basis of the concentration of lactic acid in the coronary sinus blood by comparison with the concentration of lactate in the blood of the left ventricle, it was not possible to detect any additional production of lactic acid by the myocardium under the effect of, for example, TVX 2284. In other words, it was not possible to detect any cyanide-like effect.

The tests were carried out with doses in which the compounds were fully coronary-active.

As can be seen from FIG. 1, there are not only qualitative differences, but also quantitative differences between TVX 2209 and its derivatives on the one hand and MMB on the other hand. As the Examples show, 0.5 mg of TVX 2209/kg and 0.5 mg of TVX 2284/kg are distinctly more effective than the same dose of MMB on the basis of the increase in the output of blood from the coronary sinus. Even a dose of 0.0625 mg of TVX 2209/kg has a more powerful coronary effect than the above-mentioned dose of MMB. On the basis of the extent to which output from the venous part of the coronary region is influenced, TDM (cf. FIG. 1) may also be rated as having weaker activity, because comparison with Examples TVX 2209 and TVX 2284 shows that, even in this comparison, these substances have a more powerful coronary effect in smaller doses. This applies generally to the compounds according to the invention, as shown by the comparison in FIGS. 2 and 3. It can be seen from this comparison that, on the basis of output from the coronary sinus, all the compounds subjected to exhaustive pharmacological tests are more active than TDM in the same dose. In addition, it must be pointed out that the compounds according to the invention regularly produce a reduction in heart rate (in a lower dosage in the case of TVX 2209, cf. FIG. 1), a property which TDM does not have.

The data of some of the exhaustively tested compounds are shown in Table 1. The following particulars are given:

Column 1: Example No. and test code
Column 2: Increase in circulation in the region of the coronary sinus
Column 3: Duration of activity in minutes (from column 2)
Column 4: Increase in the concentration of oxygen in the coronary sinus blood
Column 5: Duration of activity in minutes (from column 4).

The duration of activity is the period of time in minutes from the moment the substance begins to take effect to the point at which 50% of the maximum effect is reached again.

The symbols used in Table 1 have the following meaning:

| Increase/decrease | | Column 2 Blood circulation coronary sinus in % | Columns 3 and 5 Duration of activity in minutes | Column 4 $O_2$-saturation in % |
| --- | --- | --- | --- | --- |
| φ | φ | up to 10 | <5 | up to 10 |
| (+) | (−) | 10 to 20 | 5 to 15 | 10 to 20 |
| + | − | 20 to 50 | 15 to 30 | 20 to 30 |
| ++ | − − | 50 to 100 | 30 to 60 | 30 to 50 |
| +++ | − − − | 100 to 200 | 60 to 120 | 50 to 100 |
| ++++ | − − − − | over 200 | >120 | over 100 |

| 1 | 2 | 3 | 4 | 5 |
| --- | --- | --- | --- | --- |
| 16 (TVX 2209) | ++++ | ++ | +++ | +++ |
| 18 (TVX 2285) | ++++ | + | ++++ | ++ |
| 17 (TVX 2284) | +++ | +++ | +++ | +++ |
| 19 (TVX 2285) | ++++ | φ | ++++ | ++++ |
| 22 (TVX 2508) | ++++ | φ | +++ | + |
| 30 (TVX 2324) | ++++ | ++ | +++ | ++ |
| 14 (TVX 2331) | +++ | + | +++ | + |
| 25 (TVX 2314) | ++++ | + | +++ | + |
| MMB | ++++ | φ | +++ | φ |

The acute toxicity of the compounds according to the invention is low. In the case of TVX 2209, the $DL_{50}$, i.e. the dose at which 50% of the animals die after a single administration, amounts to 190 mg/kg of live weight after intravenous administration and to 1600 mg/kg after oral administration. Conversion of these values into ratios with the coronary-active doses produces very favourable therapeutic indices which should guarantee therapeutically safe handling.

The production of the compounds of general formula 1 according to the invention may be illustrated for example by the following reaction scheme:

pounds such as these are, in particular, oxides, hydroxides and carbonates or bicarbonates of alkali or alkaline earth metals or aluminium and tertiary organic amines. Potassium carbonate, triethylamine and dicyclohexyl methylamine have proved to be particularly suitable.

The reaction temperatures may be varied within a relatively wide range. Particularly suitable reaction temperatures are, temperatures in the range from 0° C. to 80° C. The reaction is generally carried out at temperatures in the range from 10° C. to 50° C., preferably at temperatures in the range from 15° C. to 30° C.

The reaction is best carried out under normal pressure.

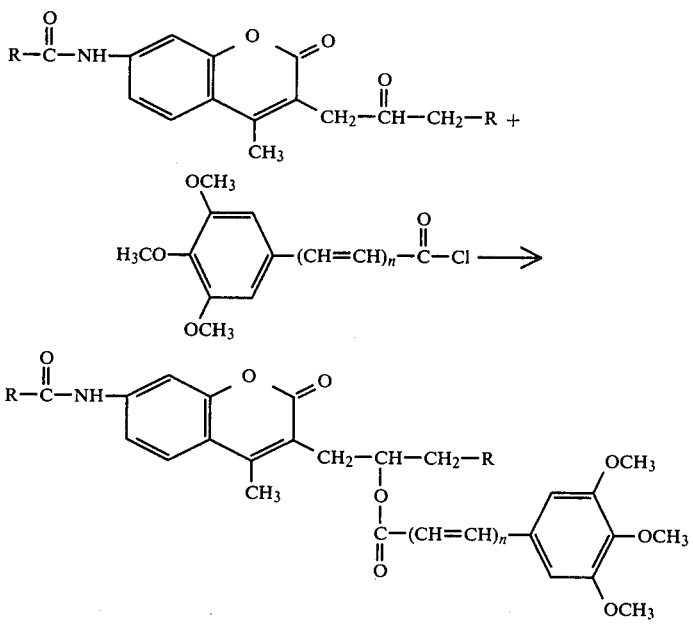

in which formulae R is as defined above and n=0 or 1. The reaction is best carried out in the presence of diluents. Suitable diluents are inert organic solvents such as halogenated hydrocarbons, for example chloroform and dichloroethane, aliphatic ketones such as, for example, acetone, methylethyl ketone or even diethyl ketone, also special solvents with a strong dipolar character. Solvents such as these include hexamethyl phosphoric acid triamide, tetrahydrofuran, dimethyl formamide and dioxane. The reaction is best carried out in the presence of condensation agents as binders for the acid liberated. Suitable acid binders include any conventional alkaline reacting inorganic and organic compounds which do not take part in the reaction. Com- In the application of the process according to the invention, from 1 to 1.5 moles of acid halide and from 1.5 to 2 moles of acid binder are used per mol of alcohol to be esterified. The reaction is best carried out with vigorous stirring and is normally complete after 30 minutes to 2 hours. The reaction mixture is worked up by mixing with water and filtering off the deposit formed. The product thus obtained is purified by recrystallisation from a suitable organic solvent.

Some of the starting compounds of general formula II are known from the literature. Where they are not already known, they are produced in accordance with the following reaction scheme:

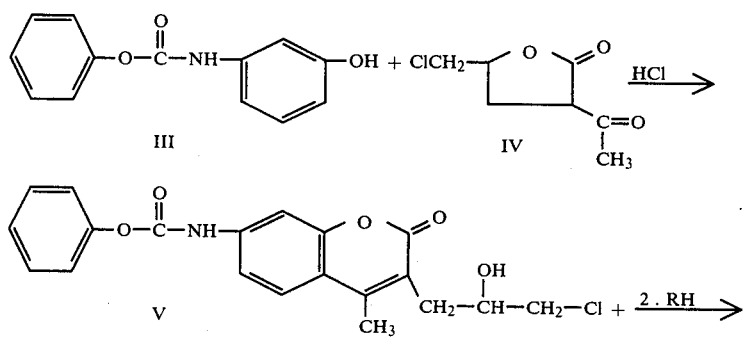

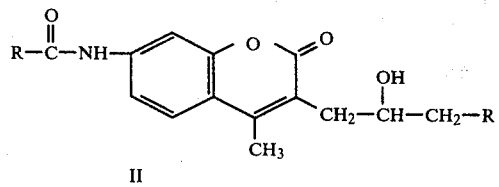

in which formulae R is as defined above. In reaction III+IV→V, IV is best used in a quantity of from 1.5 to 2.5 moles per mol of III. The reaction is best carried out in diluents. Suitable diluents include any solvents which do not themselves take part in the reaction. Preferred solvents are polar solvents, such as alcohols, preferably methanol and ethanol, aliphatic ketones, dimethyl formamide and tetrahydrofuran. The cyclising reaction is preferably carried out at low temperatures, below 0° C. Temperatures in the range from −20° C. to −50° C. are particularly preferred.

Cyclisation is obtained by saturating a solution of III and IV with hydrogen halide, and leaving the resulting saturated solution standing for several days at room temperature in a closed vessel. Working up is best carried out by diluting with water or with a mixture of water and a lower aliphatic alcohol which has been alkalised beforehand.

Purification is normally carried out by recrystallisation from a suitable organic solvent.

In the reaction V+2RH→II, from 2 to 5 moles of RH are used per mole of V. The reaction is preferably carried out in inert organic solvents such as, for example, benzene, toluene and chlorobenzene. Good yields are obtained at reaction temperatures corresponding to the boiling point of the particular solvent used. The reaction is normally complete after 5 to 25 hours.

The present invention also relates to pharmaceutical preparations which contain one or more active principles according to the invention in addition to non-toxic, inert pharmaceutically acceptable carriers.

In the context of the invention, pharmaceutical preparations are tablets, capsules, dragees, granulates, suppositories, solutions, suspensions, emulsions and sprays. Pharmaceutical carriers include fillers and diluents (for example starches, lactose, cane sugar, glucose, mannitol and silica); binders (for example carboxymethyl cellulose, alginates, gelatin and polyvinyl pyrrolidone); humectants (for example glycerol); release agents (for example agar-agar, calcium carbonates and sodium bicarbonates); solution retarders (for example paraffin); resorption accelerators (for example quaternary ammonium compounds); wetting agents (for example cetyl alcohol and glycerol monostearate), absorbents (for example kaolin and bentonite) and lubricants (for example talcum, calcium and magnesium stearate and polyethylene glycols). Suppositories may additionally contain water-insoluble carriers, such as for example polyethylene glycols, fats and esters of relatively long-chain carboxylic acids and alcohols (for example $C_{14}$-alcohol and $C_{16}$-fatty acid). Solutions and emulsions may additionally contain diluents (for example water and alcohols) and suspending agents (for example ethoxylated isostearyl alcohols, polyoxyethylene sorbitol and sorbitan esters, bentonite and agar-agar).

Colorants, preservatives and also odoriferous substances and flavourings may also be added to the above-mentioned formulations. The above-mentioned solid formulations, for example tablets, dragees and granulates, may be provided with the usual coatings and shells which may contain opacifiers.

In the case of oral formulations, the active principles may be present in a dose of from 50 to 300 mg and more especially in a dose of from 100 to 200 mg, daily doses of 3×1 to 3×2 units being envisaged. Ampoules containing from 5 to 15 mg/ml of active principle solution are intended to be used for intravenous application. Daily doses of from 1 to 2 ampoules each containing 5 ml of solution are envisaged.

The compounds according to the invention are intended for use in human medicine for the treatment of heart and vascular disorders such as, for example, coronary insufficiency and angina pectoris and accordingly represent an enrichment of pharmacy.

EXAMPLE 1

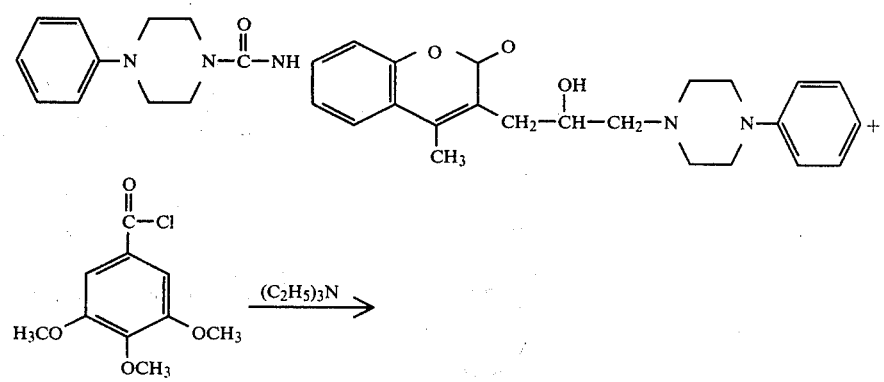

-continued

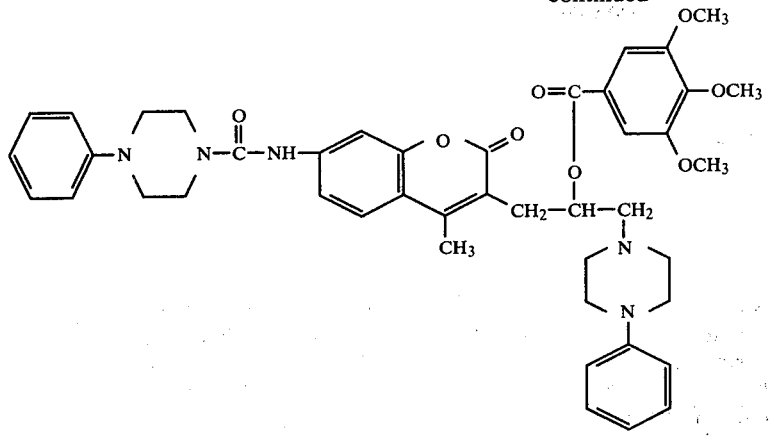

7 g (0.012 mole) of N-{3-[3-(4-phenyl-1-piperazinyl)-2-hydroxypropyl]-4-methyl-2-oxo-2H-1-benzopyran-7-yl}-4-phenyl-1-piperazinyl carboxamide are dissolved in 50 ml of absolute hexamethyl phosphoric acid triamide, followed by the addition of 1.8 ml (0.0132 mole) of triethylamine. A solution of 3.1 g (0.0132 mole) of 3,4,5-trimethoxybenzoyl chloride in 50 ml of absolute acetone is then added dropwise at room temperature. After stirring for about 30 minutes, the mixture is poured into 1 liter of water and the crystalline deposit formed is filtered off under suction. It is taken up in chloroform, the chloroform solution is washed twice with water and then dried over sodium sulphate.

After chromatography on silica gel and elution with chloroform/ethanol (95:5), concentration by evaporation and recrystallisation from ethylacetate, N-{3-[3-(4-phenyl-1-piperazinyl)-2-(3,4,5-trimethoxybenzoyloxy)-propyl]-4-methyl-2-oxo-2H-1-benzopyran-7-yl}-4-phenyl-1-piperazinyl carboxamide, which melts at 237° C. with decomposition, is obtained in a yield of 6.2 g (corresponding to 66.7% of the theoretical).

Analysis for $C_{44}H_{49}N_5O_8$: calculated: C 68.11%, H 6.37%, N 9.03%; observed: C 68.00%, H 6.40%, N 8.70%.

The compounds listed in Table 2:

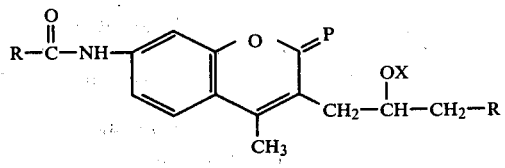

in which X is either the 3,4,5-trimethoxybenzoyl radical (represented as A in the Table) or the 3,4,5-trimethoxycinnamoy radical (represented as B in the Table), were produced in accordance with Example 1.

Table 2

| Example | R | X | Analysis in % calculated (c) observed (o) C | H | N | M.p. in °C. | Yield in % | Proton acceptor (auxiliary base) |
|---|---|---|---|---|---|---|---|---|
| 2 | piperidin-1-yl | B | c:66.75 o:67.00 | 7.00 7.10 | 6.49 6.50 | 133 | 60.8 | $(C_2H_5)_3N$ |
| 3 | 4-phenylpiperazin-1-yl | B | c:68.90 o:69.90 | 6.41 6.30 | 8.73 8.75 | 218 decomp. | 53 | " |
| 4 | 3,5-dimethylmorpholin-4-yl | B | c:64.48 o:64.40 | 6.97 7.20 | 5.93 5.70 | 233.5–235.5 | 41 | " |
| 5 | 3,5-dimethylmorpholin-4-yl | A | c:63.42 o:62:90 | 6.95 6.90 | 6.16 5.90 | 185–187 | 61.3 | $(C_2H_5)_3N$ |
| 6 | 4-methylpiperidin-1-yl | B | c:67.53 o:67.20 | 7.31 7.40 | 6.22 5.80 | 147–148 | 68 | " |

Table 2-continued

| Example | R | X | Analysis in % calculated (c) observed (o) C | H | N | M.p. in °C | Yield in % | Proton acceptor (auxiliary base) |
|---|---|---|---|---|---|---|---|---|
| 6a | H₃C—[piperidine]N— maleate | | c:63.70 o:63.77 | 6.75 6.83 | 5.31 5.17 | 147 to 148 decomp. | — | — |
| 7 | H₃C—[piperidine]N— | A | c:66.54 o:67.10 | 7.29 7.30 | 6.47 6.40 | 159–160 | 68 | (C₂H₅)₃N |
| 8 | [piperidine]N— | A | c:65.68 o:65.50 | 6.97 7.00 | 6.76 6.50 | 173 | 67 | " |
| 9 | (CH₂=CH—CH₂)₂N— | B | c:67.94 o:67.70 | 6.75 6.90 | 6.26 610 | 133 | 67.6 | " |
| 10 | (C₂H₅)₂N— | A | c:64.30 o:64.70 | 7.25 7.20 | 7.03 7.00 | 155 | 67.4 | " |
| 11 | (C₂H₅)₂N— | B | c:65.47 o:65.30 | 7.27 7.40 | 6.74 6.60 | 168 | 57 | " |
| 12 | [phenyl]—CH₂—N(CH₃)— | A | c:69.25 o:69.20 | 6.25 6.20 | 6.06 5.90 | 167 | 80 | (C₂H₅)₃N |
| 13 | [phenyl]—CH₂—N(CH₃)— | B | c:70.08 o:70.40 | 6.30 6.30 | 5.84 5.70 | 179 | 80.5 | " |
| 14 | [cyclohexyl]—N(CH₃)— | A | c:67.33 o:67.70 | 7.58 7.80 | 6.20 5.90 | 136 | 67 | " |
| 15 | [cyclohexyl]—N(CH₃)— | B | c:68.26 o:67.90 | 7.59 7.40 | 5.97 6.00 | 146 | 54 | " |
| 16 | O[morpholine]N— | A | c:61.43 o:61.32 | 6.72 6.47 | 6.72 6.77 | 198 | 61 | " |
| 16a | O[morpholine]N— hydrochloride | | c:58.05 o:58.10 | 6.00 6.20 | 6.35 6.20 | >200 | — | — |
| 16b | O[morpholine]N— sulphate | | c56.96 o:56.63 | 5.98 6.27 | 6.23 6.04 | 172 to 174 decomp. | — | — |
| 16c | O[morpholine]N— D,L-camphor-10-sulphonate | | c:58.60 o:58.23 | 6.46 6.40 | 4.90 4.56 | >128 | — | — |

Table 2-continued

| Example | R | | X | Analysis in % calculated (c) observed (o) | | | M.p. in °C. | Yield in % | Proton acceptor (auxiliary base) |
|---|---|---|---|---|---|---|---|---|---|
| | | | | C | H | N | | | |
| 17 | morpholino | | B | c:62.66<br>o:62.20 | 6.34<br>6.20 | 6.45<br>6.40 | 185 decomp | 51 | $(C_6H_{11})_2NCH$ |
| 17a | morpholino<br>hydrobromide | | | c:55.74<br>o:55.76 | 4.78<br>6.00 | 5.73<br>5.49 | >220 | — | — |
| 17b | morpholino<br>maleate | | | c:59.45<br>o:59.40 | 5.91<br>6.07 | 5.47<br>5.35 | 137 to 140 de-comp. | — | — |
| 17c | morpholino<br>hydrogen sulphate | | | c:54.46<br>o:54.88 | 5.78<br>5.82 | 5.60<br>5.74 | 101 de-comp. | — | — |
| 17d | morpholino<br>p-toluene-sulphonate hydrate | | | c:58.49<br>o:58.55 | 6.11<br>6.23 | 4.99<br>4.89 | 148 to 153 de-comp. | — | — |
| 17e | morpholino<br>oxylate hydrate | | | c:56.91<br>o:57.19 | 5.97<br>5.70 | 5.53<br>5.62 | 156 to 158 | — | — |
| 17f | morpholino<br>methane sulphonate | | | c:56.21<br>o:56.20 | 6.07<br>6.05 | 5.62<br>5.52 | 230 de-comp. | — | — |
| 17g | morpholino<br>naphthaline-(1,5)-disulphonate | | | c:58.86<br>o:58.74 | 5.70<br>5.87 | 5.28<br>5.21 | >200 | — | — |
| 17h | morpholino<br>hydrochloride | | | c:59.34<br>o:59.21 | 6.15<br>6.21 | 6.11<br>6.11 | 190 | — | — |
| 18 | piperidino | | A | c:66.54<br>o:66.60 | 7.29<br>7.50 | 6.47<br>6.40 | 180 | 63 | $(C_6H_{11})_2NCH_3$ |

TABLE 2-continued

|  |  |  | Analysis in % calculated (c) observed (o) | | | | | Proton acceptor (auxiliary |
|---|---|---|---|---|---|---|---|---|
| Example | R | X | C | H | N | M.p. in °C. | Yield in % | base) |
| 19 | (azepane, N-) | B | c:67.53<br>o:67.50 | 7.31<br>7.30 | 6.22<br>6.10 | 134.6 | 56.7 | " |
| 20 | (pyrrolidine, N-) | A | c:64.74<br>o:64.70 | 6.62<br>6.60 | 7.08<br>7.20 | 206 de-comp. | 68 | " |
| 21 | (pyrrolidine, N-) | B | c:65.90<br>o:65.60 | 6.67<br>6.90 | 6.78<br>6.90 | 151 | 73.3 | " |
| 22 | (n-C$_4$H$_9$)$_2$N— | A | c:67.67<br>o:67.40 | 8.38<br>8.50 | 5.92<br>5.80 | 123 | 48 | (C$_6$H$_{11}$)$_2$NCH$_3$ |
| 23 | (n-C$_4$H$_9$)$_2$N— | B | c:68.54<br>o:68.20 | 8.36<br>7.90 | 5.71<br>5.80 | 105 | 58 | " |
| 24 | (CH$_2$=CH—CH$_2$)$_2$N— | A | c:66.96<br>o:66.80 | 6.71<br>6.60 | 6.50<br>6.20 | 118 | 69.4 | (C$_2$H$_5$)$_3$N |
| 25 | (2-ethylpiperidine, N-) | A | c:67.33<br>o:67.20 | 7.58<br>7.40 | 6.20<br>5.90 | 93–96 | 30 | K$_2$CO$_3$ |
| 26 | (2-ethylpiperidine, N-) | B | c:68.25<br>o:68.20 | 7.59<br>7.60 | 5.97<br>6.20 | 101–103 | 57 | (C$_2$H$_5$)$_3$N |
| 27 | (4-methylpiperazine, N-) | A | c:62.66<br>o:62.30 | 6.96<br>6.70 | 10.74<br>10.30 | 185–187 | 35 | Amberlyst A 26 |
| 28 | A—O—CH$_2$—CH$_2$—N(CH$_3$)— | A | c:60.66<br>o:60.20 | 6.01<br>5.90 | 4.24<br>4.40 | 70–72 | 70 | (C$_2$H$_5$)$_3$N |
| 29 | O—CH$_2$—CH$_2$—N(CH$_3$)— | B | c:62.97<br>o:62.15 | 6.13<br>6.19 | 3.93<br>3.77 | 86–88.5 (indefinite) | 49 | " |
| 30 | (4-methylpiperazine, N-) | B | c:63.79<br>o:63.70 | 6.99<br>7.00 | 10.33<br>10.00 | 110 | 30 | Amberlyst |
| 31 | (2,6-dimethylpiperidine, N-) | A | c:67.34<br>o:67.37 | 7.58<br>7.56 | 6.20<br>6.17 | 178 | 52 | (C$_2$H$_5$)$_3$N |
| 32 | (2,6-dimethylpiperidine, N-) | B | c:68.26<br>o:68.17 | 7.59<br>7.56 | 5.97<br>5.78 | 156 | 50 | (C$_2$H$_5$)$_3$N |
| 33 | —N(CH$_3$)—(CH$_2$—CH$_2$—O)$_2$—Z | A | c:60.16<br>o:60.10 | 6.26<br>6.41 | 3.90<br>3.92 | 58° | 45 | (C$_2$H$_5$)$_3$N |

Table 2-continued

| Example | R | | Analysis in % calculated (c) observed (o) | | | | | Proton acceptor (auxiliary |
|---|---|---|---|---|---|---|---|---|
| | | X | C | H | N | M.p. in °C. | Yield in % | base) |
| | 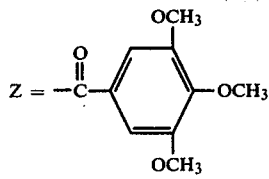 | | | | | | | |

EXAMPLE 34

The production of a number of starting compounds of formula II is described in this Example.

(a)

230 g (1 mole) of 3-hydroxyphenyl carbamic acid phenyl ester and 300 g (1.7 mole) of 3-acetyl-5-chloromethyl-2-oxotetrahydrofuran were dissolved in 2 liters of absolute ethanol and 100 ml of absolute dimethyl formamide and the resulting solution saturated with hydrogen chloride at −40° C. After standing for 3 days at room temperature, the deposit formed was filtered off under suction, washed first with aqueous methanol containing sodium bicarbonate and then with pure methanol. Recrystallization from dichloroethane/isopropanol (4:1) gave 252 g (65% of the theoretical) of N-[3-(3-chloro-2-hydropropyl)-4-methyl-2-oxo-2H-1-benzopyran-7-yl]-carbamic acid phenyl ester melting at 208° to 210° C.

Analysis for $C_{20}H_{18}ClNO_5$ (387.829): calculated: C 62.00%, H 4.66%, Cl 9.12%, N 3.61%; observed: C 61.00%, H 4.70%, Cl 9.30%, N 3.20%.

(b)

N-[3-(3-Morpholino-2-hydroxypropyl)-4-methyl-2-oxo-2H-1-benzopyran-7-yl]-morpholino carboxamide

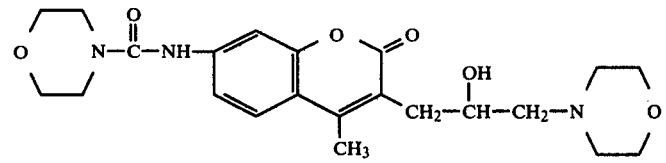

61.6 g (=0.0556 mole) of N-[3-(3-chloro-2-hydroxypropyl)-4-methyl-2-oxo-2H-1-benzopyran-7-yl]-carbamic acid phenyl ester and 33.9 g (0.39 mole) of morpholine were dissolved in 200 ml of chlorobenzene, 6.4 g (0.06 mole) of sodium carbonate added and the mixture boiled for about 15 hours. The deposit precipitated was then filtered off under suction and washed intensively in 50% aqueous ethanol. Drying in vacuo gave 17.8 g (74.1% of the theoretical) of N-[3-(3-morpholino-2-hydroxypropyl)-4-methyl-2-oxo-2H-1-benzopyran-7-yl]-morpholinocarboxamide which decomposes above 220° C.

(c)

The compounds listed in Table 3 were similarly obtained:

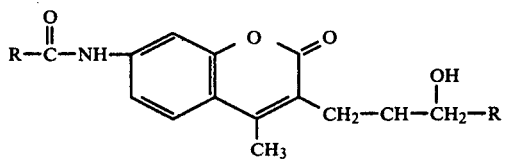

Table 3

| R | Analysis in % calculated (c) observed (o) | | | M.p. in °C. | Yield in % |
|---|---|---|---|---|---|
| | C | H | N | | |
| ![piperidine with C2H5] N— with C₂H₅ | c:69.53 8.55 8.69<br>o:69.30 8.20 8.40 | | | 149.5–150.5 | 66 |
| $(C_2H_5)_2N-$ | c:65.48 8.24 10.42<br>o:65.45 8.40 10.35 | | | 149 | 26.5 |
| $(CH_2=CH-CH_2)_2N-$ | c:69.15 7.37 9.51<br>o:68.90 7.60 9.50 | | | 97 | 41 |

Table 3-continued

| R | C (c/o) | H | N | M.p. in °C. | Yield in % |
|---|---|---|---|---|---|
| H₃C-morpholine-N— (2,6-dimethylmorpholino) | c:64.00<br>o:63.80 | 7.65<br>7.60 | 8.60<br>8.60 | 209–210 | 60 |
| H₃C-piperidine-N— (4-methylpiperidino) | c:68.54<br>o:69.02 | 8.19<br>8.21 | 9.22<br>8.98 | 207 decomp. | 70 |
| hexahydroazepino-N— | c:68.54<br>o:68.30 | 8.19<br>8.20 | 9.22<br>9.20 | 211 | 55 |
| cyclohexyl-N(CH₃)— | c:69.54<br>o:69.10 | 8.54<br>8.55 | 8.69<br>8.80 | 200 | 65 |
| (n-C₄H₉)₂N— | c:69.86<br>o:70.10 | 9.58<br>9.50 | 8.15<br>8.00 | 120 | 52 |
| C₆H₅—CH₂—N(CH₃)— | c:72.12<br>o:71.95 | 6.66<br>6.45 | 8.41<br>8.45 | 195 | 67 |
| Z—(O—CH₂—CH₂)₂—N(CH₃)— | c:58.17<br>o:58.05 | 7.52<br>7.49 | 8.48<br>8.53 | 96–98 | 57 |

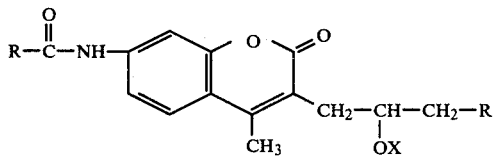

$$Z = -\overset{O}{\underset{\|}{C}}-\text{C}_6\text{H}_2(\text{OCH}_3)_3$$

What is claimed is:

1. A 2-benzopyranone compound of the formula $$R-\overset{O}{\underset{\|}{C}}-NH-\text{[benzopyranone]}-CH_2-CH(OX)-CH_2-R$$

(with CH₃ substituent)

wherein
X is a 3,4,5-trimethoxybenzoyl group or a 3,4,5-trimethoxycinnamoyl group; and each
R individually is selected from the group consisting of C₁–C₆ alkylamino and C₁–C₆ dialkylamino in which one hydrogen atom may be replaced by a hydroxyl group which may in turn be esterifed with a 3,4,5-trimethoxybenzoyl or 3,4,5-trimethoxycinnamoyl group; amino substituted once or twice by C₂–C₄ alkenyl, aralkyl of up to 10 carbon atoms, or C₄–C₇ cycloalkyl; or an N-containing heterocyclic ring which is a member of the group consisting of pyrrolidino, piperidino and hexahydroazepino and which are linked through a nitrogen atom and which heterocyclic ring may be substituted by phenyl, alkyl or hydroxyalkyl wherein the hydroxy group may be esterified by a 3,4,5-trimethoxy benzoyl or 3,4,5-trimethoxy cinnamoyl group;

or a salt of each compound with a physiologically acceptable acid.

2. 2-Benzopyranone compound as claimed in claim 1 designated N-{3-[3-piperidino-2-(3,4,5-trimethoxycinnamoyloxy)-propyl]-4-methyl-2-oxo-2H-1-benzopyran-7-yl}-1-piperidinocarboxamide or a pharmaceutically acceptable salt thereof.

3. 2-Benzopyranone compound as claimed in claim 1 designated N-{3-[3-(4-methylpiperidino)-2-(3,4,5-trimethoxybenzoyloxy)-propyl]-4-methyl-2-oxo-2H-1-benzofuran-7-yl}-4-methyl-1-piperidinocarboxamide or a pharmaceutically acceptable salt thereof.

4. 2-Benzopyranone compound as claimed in claim 1 designated N-{3-[3-piperidino-2-(3,4,5-trimethoxybenzoyloxy)-propyl]-4-methyl-2-oxo-2H-1-benzopyran-7-yl}-1-piperidinocarboxamide or a pharmaceutically acceptable salt thereof.

5. 2-Benzopyranone compound as claimed in claim 1 designated N-{3-[3-diallylamino-2-(3,4,5-trimethoxycinnamoyloxy)-propyl]-4-methyl-2-oxo-2H-1-benzopyran-7-yl}-N',N'-diallyl urea or a pharmaceutically acceptable salt thereof.

6. 2-Benzopyranone compound as claimed in claim 1 designated N-{3-[3-diethylamino-2-(3,4,5-trimethoxybenzoyloxy)-propyl]-4-methyl-2-oxo-2H-1-benzopyran-7-yl}-N',N'-diethyl urea or a pharmaceutically acceptable salt thereof.

7. 2-Benzopyranone compound as claimed in claim 1 designated N-{3-[3-diethylamino-2-(3,4,5-trimethoxycinnamoyloxy)-propyl]-4-methyl-2-oxo-2H-1-benzopyran-7-yl}-N',N'-diethyl urea or a pharmaceutically acceptable salt thereof.

8. 2-Benzopyranone compound as claimed in claim 1 designated N-{3-[3-(methylbenzylamino)-2-(3,4,5-trimethoxybenzoyl oxy)-propyl]-4-methyl-2-oxo-2H-1-benzopyran-7-yl}-N'-benzyl-N'-methyl urea or a pharmaceutically acceptable salt thereof.

9. 2-Benzopyranone compound as claimed in claim 1 designated N-{3-[3-(methylbenzylamino)-2-(3,4,5-trimethoxycinnamoyloxy)-propyl]-4-methyl-2-oxo-2H-1-benzopyran-7-yl}-N'-benzyl-N'-methyl urea of a pharmaceutically acceptable salt thereof.

10. 2-Benzopyranone compound as claimed in claim 1 designated N-{3-[3-(cyclohexylmethylamino)-2-(3,4,5-trimethoxybenzoyloxy)-propyl]-4-methyl-2-oxo-2H-1-benzopyran-7-yl}-N'-cyclohexyl-N'-methyl urea of a pharmaceutically acceptable salt thereof.

11. 2-Benzopyranone compound as claimed in claim 1 designated N-{3-[3-(methylcyclohexylamino)-2-(3,4,5-trimethylcinnamoyl propyl]-4-methyl-2-oxo-2H-1-benzopyran-7-yl}-N'-cyclohexyl-N'-methyl urea or a pharmaceutically acceptable salt thereof.

12. 2-Benzopyranone compound as claimed in claim 1 designated N-{3-[3-hexahydroazepino-2-(3,4,5-trimethoxybenzoyl)propyl[-4-methyl-2-oxo-2H-1-benzopyran-7-yl}-1-hexahydroazepino carboxamide or a pharmaceutically acceptable salt thereof.

13. 2-Benzopyranone compound as claimed in claim 1 designated N-{3-[3-hexahydroazepino-2-(3,4,5-trimethoxycinnamoyl)-propyl]-4-methyl-2-oxo-2H-1-benzopyran-7-yl}-1-hexahydroazepino carboxamide or a pharmaceutically acceptable salt thereof.

14. 2-Benzopyranone compound as claimed in claim 1 designated N-{3-[3-pyrrolidino-2-(3,4,5-trimethoxybenzoyloxy)-propyl]-4-methyl-2-oxo-2H-1-benzopyran-7-yl}-1-pyrrolidinocarboxamide or a pharmaceutically acceptable salt thereof.

15. 2-Benzopyranone compound as claimed in claim 1 designated N-{3-[3-pyrrolidino-2-(3,4,5-trimethoxycinnamoyloxy)-propyl]-4-methyl-2-oxo-2H-1-benzopyran-7-yl}-1-pyrrolidinocarboxamide or a pharmaceutically acceptable salt thereof.

16. 2-Benzopyranone compound as claimed in claim 1 designated N-{3-[3-di-n-butylamino-2-(3,4,5-trimethoxybenzoyloxy)-propyl]-4-methyl-2-oxo-2H-1-benzopyran-7-yl}-N',N'-di-n-butyl urea or a pharmaceutically acceptable salt thereof.

17. 2-Benzopyranone compound as claimed in claim 1 designated N-{3-[3-di-n-butylamino-2-(3,4,5-trimethoxycinnamoyloxy)-propyl]-4-methyl-2-oxo-2H-1-benzopyran-7-yl}-N',N'-di-n-butyl urea or a pharmaceutically acceptable salt thereof.

18. 2-Benzopyranone compound as claimed in claim 1 designated N-{3-[3-diallylamino-2-(3,4,5-trimethoxybenzoyloxy)-propy]-4-methyl-2-oxo-2H-1-benzopyran-7-yl}-N',N'-diallyl urea or a pharmaceutically acceptable salt thereof.

19. 2-Benzopyranone compound as claimed in claim 1 designated N-{3-[3-(2-ethylpiperidino)-2-(3,4,5-trimethoxybenzoyloxy)propyl]-4-methyl-2-oxo-2H-1-benzopyran-7-yl}-2-ethyl-1-piperidinocarboxamide or a pharmaceutically acceptable salt thereof.

20. 2-Benzopyranone compound as claimed in claim 1 designated N-{3-[3-(2-ethylpiperidino)-2-(3,4,5-trimethoxycinnamoyloxy)propyl]-4-methyl-2-oxo-2H-1-benzopyran-7-yl}-2-ethyl-1-piperidinocarboxamide or a pharmaceutically acceptable salt thereof.

21. 2-Benzopyranone compound as claimed in claim 1 designated N-{3-[3-(N-methyl-N-(3,4,5-trimethoxybenzoyloxyethyl)-amino)-2-(3,4,5-trimethoxybenzoyloxy)-propyl]-4-methyl-2-oxo-2H-1-benzopyran-7-yl}-N'-methyl-N'-(3,4,5-trimethoxybenzoyloxyethyl) urea or a pharmaceutically acceptable salt thereof.

22. 2-Benzopyranone compound as claimed in claim 1 designated N-{3-[3-(N-methyl-N-(3,4,5-trimethoxycinnamoyloxyethyl)-amino)-2-(3,4,5-trimethoxycinnamoyloxy)-propyl]-4-methyl-2-oxo-2H-1-benzopyran-7-yl}-N'-methyl-N'-(3,4,5-trimethylcinnamoyloxyethyl) urea or a pharmaceutically acceptable salt thereof.

23. 2-Benzopyranone compound as claimed in claim 1 designated N-{3-[3-(N-methyl-N-(3,4,5-trimethoxybenzoyloxyethoxyethyl)-amino)-2-(3,4,5-trimethoxybenzoyloxy)-propyl]-4-methyl-2-oxo-2H-1-benzopyran-7-yl}-N'-methyl-N'-(3,4,5-trimethoxycinnamoyloxyethoxyethyl) urea or a pharmaceutically acceptable salt thereof.

24. 2-Benzopyranone compound as claimed in claim 1 designated N-{3-[3-(N-methyl-N-(3,4,5-trimethoxycinnamoyloxyethoxyethyl)amino)-2-(3,4,5-trimethoxycinnamoyloxy)-propyl]-4-methyl-2-oxo-2H-1-benzopyran-7-yl}-N'-methyl-N'-(3,4,5-trimethoxycinnamoyloxyethoxyethyl) urea or a pharmaceutically acceptable salt thereof.

25. A 2-benzopyranone compound of the formula of claim 1 wherein
R is hexahydroazepine 26. A 2-benzopyranone compound as claimed in claim 25 wherein X is 3,4,5-trimethoxybenzoyl.

27. A 2-benzopyranone compound as claimed in claim 25 wherein X is 3,4,5-trimethoxycinnamoyl.

28. 2-Benzopyranone compound as claimed in claim 1, wherein both R groups are identical.

29. 2-Benzopyranone compound as claimed in claim 1 wherein each R group is different from the other R group.

30. 2-Benzopyranone compound as claimed in claim 1 wherein one of the R groups is mono-alkylamino of from 1 to 6 carbon atoms in the alkyl group.

31. 2-Benzopyranone compound as claimed in claim 1 wherein one of the R groups is dialkylamino with up to 6 carbon atoms in each alkyl moiety.

32. 2-Benzopyranone compound as claimed in claim 1 wherein one of the R groups is hydroxyalkylamino or hydroxydialkylamino of up to 6 carbon atoms in each alkyl moiety.

33. 2-Benzopyranone compound as claimed in claim 1 wherein one of the R groups is hydroxyalkylamino wherein the hydroxyl group is esterified with a 3,4,5-trimethoxy benzoyl or 3,4,5-trimethoxycinnamoyl group.

34. 2-Benzopyranone compound as claimed in claim 1 wherein one of the R groups is hydroxydialkylamino esterified with a 3,4,5-trimethoxybenzoyl or a 3,4,5-trimethoxy cinnamoyl group.

35. 2-Benzopyranone compound as claimed in claim 1, wherein one of the R groups is alkenylamino of from 2 to 4 carbon atoms.

36. 2-Benzopyranone compound as claimed in claim 1 wherein one of the R groups is aralkylamino of up to 10 carbon atoms.

37. 2-Benzopyranone compound as claimed in claim 1 wherein one of the R groups is cycloalkylamino wherein the cycloalkyl moiety contains from 4 to 7 carbon atoms.

38. 2-Benzopyranone compound as claimed in claim 1 wherein one of the R groups is a pyrrolidino group.

39. 2-Benzopyranone compound as claimed in claim 1 wherein one of the R groups is a piperidino group.

* * * * *

UNITED STATES PATENT AND TRADEMARK OFFICE
CERTIFICATE OF CORRECTION

PATENT NO. : 4,241,207
DATED : Dec. 23, 1980
INVENTOR(S) : Karl-Heinz Boltze et al It is certified that error appears in the above—identified patent and that said Letters Patent is hereby corrected as shown below:

Column 6, Line 56    Insert --Table 1
                     Influence on coronary circulation
                     in anaesthetised dogs after intravenous
                     administration: dose: 2 mg/kg--.

Column 6, Line 61    Delete "2285" and insert --2283--.

Column 6, Line 63    Delete "2508" and insert --2308--.

Column 13, Example 9 Delete "610" and insert --6.10--.
          Column 6

Column 13, Example 16a Delete "6.00" and insert --6.09--.

Column 15, Example 17c Delete "101" and insert --191--.

Signed and Sealed this

Fourth Day of August 1981

[SEAL]

Attest:

GERALD J. MOSSINGHOFF

Attesting Officer   Commissioner of Patents and Trademarks